United States Patent
Au et al.

(10) Patent No.: US 11,274,075 B2
(45) Date of Patent: Mar. 15, 2022

(54) DEFI AND TAURATE AMIDE MIXTURES AND PROCESSES THEREOF

(71) Applicant: Conopeo, Inc., Englewood Cliffs, NJ (US)

(72) Inventors: Van Au, Oxford, CT (US); Bijan Harichian, Brookfield, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 433 days.

(21) Appl. No.: 16/336,805

(22) PCT Filed: Sep. 6, 2017

(86) PCT No.: PCT/EP2017/072312
§ 371 (c)(1),
(2) Date: Mar. 26, 2019

(87) PCT Pub. No.: WO2018/059889
PCT Pub. Date: Apr. 5, 2018

(65) Prior Publication Data
US 2021/0284605 A1    Sep. 16, 2021

(30) Foreign Application Priority Data
Sep. 28, 2016  (EP) .................................... 16191203

(51) Int. Cl.
*C07C 303/22*   (2006.01)
*B01J 23/02*    (2006.01)
*B01J 23/06*    (2006.01)
*C11D 1/28*     (2006.01)

(52) U.S. Cl.
CPC ............. *C07C 303/22* (2013.01); *B01J 23/02* (2013.01); *B01J 23/06* (2013.01); *C11D 1/28* (2013.01)

(58) Field of Classification Search
CPC ... C07C 303/22; C07C 303/32; C07C 309/03; C07C 309/15; C11D 1/12; C11D 1/28
See application file for complete search history.

(56) References Cited

U.S. PATENT DOCUMENTS

| | | | | |
|---|---|---|---|---|
| 4,405,526 A | * | 9/1983 | Lamberti | C07C 303/22 554/92 |
| 4,536,338 A | * | 8/1985 | Urban | C07C 303/22 554/92 |
| 6,013,616 A | * | 1/2000 | Fabry | A61K 8/44 510/127 |
| 6,562,874 B1 | * | 5/2003 | Ilardi | C07C 303/22 510/156 |
| 2005/0071931 A1 | | 4/2005 | Yoshida et al. | |
| 2009/0062406 A1 | | 3/2009 | Loeffler | |
| 2012/0141389 A1 | * | 6/2012 | Cotrell | A61Q 11/00 424/54 |

FOREIGN PATENT DOCUMENTS

CN           101375826         3/2009

OTHER PUBLICATIONS

HunterLab, Applications Note, Insight on Color, Hunter L, A,B Color Scale, vol. 8, No. 9, pp. 1-4 (Year: 2008).*
Search Report and Written Opinion in PCTEP2017072312; dated Nov. 20, 2017.
IPRP2 in PCTEP2017072312.
Search Report and Written Opinion in EP16191203; dated Feb. 15, 2017.

* cited by examiner

*Primary Examiner* — Yate' K Cutliff
(74) *Attorney, Agent, or Firm* — Krista A. Kostiew

(57) ABSTRACT

The invention comprises a process for preparing mixtures of DEFI and amide taurate (ATA) having excellent yields of ATA and substantial absence of browning of final ATA and DEFI mixtures. The process permits much greater flexibility in ratios of DEFI to ATA. The invention further relates to mixtures prepared by processes of the invention.

9 Claims, No Drawings

DEFI AND TAURATE AMIDE MIXTURES AND PROCESSES THEREOF

CROSS-REFERENCE TO RELATED APPLICATIONS

This application is a U.S. national phase application under 35 U.S.C. § 371 of International Application No. PCT/EP2017/072312, filed on Sep. 6, 2017, which claims priority to European Patent Office Application No. 16191203.5, filed Sep. 28, 2016, the entire disclosures of which are incorporated herein by reference in their entireties, for any and all purposes.

FIELD OF THE INVENTION

The present invention relates to compositions comprising mixtures of directly esterified fatty acyl isethionate ("DEFI") and alkyl taurate amides ("ATA") made from the amidation of taurines (e.g., N-methyl taurine); further, it relates to a process for making the mixtures in a single reactor, preferably in a DEFI reactor. The invention further relates to mixtures made by the process of the invention. Controlling order of addition permits processes to be conducted at lower temperatures than previously believed required to drive yield of DEFI which in turn permits production of higher yields of ATA as well as substantial elimination of browning. The low temperature reaction further permits far greater flexibility in production of desired blends of DEFI and ATA.

BACKGROUND OF THE INVENTION

A common anionic surfactant used in personal care and personal wash compositions is acyl isethionate. The compound is milder than soap, yet retains characteristics which consumers associate with good cleansing (e.g., foaming).

The acyl isethionate surfactant is commonly produced by the direct esterification of a fatty acid (e.g., $C_{10}$ to $C_{16}$ fatty acid such as lauric acid) and isethionate (e.g., $OHCH_2CH_2SO_3^-Na^+$) in a process commonly known as the "DEFI" process. The DEFI process is conducted in a single DEFI reactor.

Another commonly used anionic surfactant are alkyl taurate amides (e.g., N-methyl taurate). Alkyl taurate amides are also well known anionic surfactants which provide good foam.

In general, ATA may be manufactured by reaction of a taurine; or a taurate salt (e.g., $NH_2 CH_2CH_2SO_3^-M^+$, where $M^+$ may be, for example, sodium or potassium counterion); with the appropriate fatty acid.

For example, sodium methyl stearoyl taurate can be made by heating triple-pressed stearic acid, sodium methyl taurate solution, and boric acid to 200° C. while stirring with a subsurface nitrogen purge and distilling off water. In such process, as described in the literature, stirring continues at 195-200° C. for six hours at atmospheric pressure, and then three hours at 100 mm Hg vacuum. The mass is cooled and the resulting product, an off-white waxy solid, is ground to powder. The product is reported to be 64.0% sodium methyl stearoyl taurate as active ingredient, 29.5% free fatty acid, 2.5 sodium N-methyl taurate, and 4.0% other unspecified chemicals. Conversion of sodium methyl taurate was reported at greater than 91%. Using coconut fatty acid instead of stearic acid resulted in 97% conversion.

While DEFI and ATA can be separately made and combined, it would be far more economical and efficient to make mixtures of the two in a single reactor, for example, in a single DEFI reactor. However, reacting, for example, both alkali metal isethionate and N-methyl taurine with fatty acid in a DEFI reactor (to produce, respectively, DEFI and ATA) results in relatively low yields of ATA and product which is "browned". If reaction temperatures are not sufficiently high, DEFI yield is compromised, but the same high temperature results in browning of the ATA. Thus, the overall L values of the DEFI/ATA mixture is much lower (more browning) compared to that made by the subject invention.

U.S. Pat. No. 6,562,874 to Ilardi et al., for example, discloses compositions in which DEFI and ATA are formed in the same reactor. Specifically, Ilardi discloses a DEFI reaction (in which isethionate is combined with fatty acid) in which amines (such as taurine) are used to partially replace isethionate (column 4, lines 49-57).

Applicants have reproduced Examples 26-31, Table 4, of U.S. Pat. No. 6,562,874 to Ilardi et al. and demonstrated that, at temperatures typically required to drive DEFI reaction yields (e.g., 238° C. in all examples), yields are quite low. Various additional comparative examples further demonstrate that, at these temperatures, bars are much darker.

Unexpectedly, applicants have found that, if only taurine is combined initially with fatty acid (allowing pre-production of ATA before adding most or all of the isethionate), and temperature is maintained relatively low (e.g., 200° C. or less, preferably 180 to 195° C.), the resulting ATA is believed (without wishing to be bound by theory) to act as emulsifier. Thus, when the bulk or all of the alkali metal isethionate is added to ATA and residual fatty acids (to produce DEFI and resulting DEFI/ATA mixtures), the temperature of this portion of the reaction can also be maintained relatively low (e.g., 200° C. or less, preferably 180 to 195° C.). In this way, yields of ATA (produced in first part of reaction) are much higher than when DEFI and ATA are entirely produced simultaneously (as in Ilardi), while, simultaneously (because second part of reaction where majority or all DEFI is produced is done at much lower temperature), browning of ATA is avoided and L value of overall DEFI/ATA mixture is much higher than previously possible.

BRIEF DESCRIPTION OF THE INVENTION

In one aspect, the present invention thus comprises a process for making mixtures of DEFI and alkyl taurate amides in a single reactor, and wherein alkyl taurate amide is made in high yields (75% or greater, preferably 80% or greater) and wherein, after the bulk or all of the DEFI is produced in the second portion of the reaction, ATA is substantially free of browning (e.g., as defined by L value of the DEFI/ATA mixture of 80 or greater, preferably 80 to 100, more preferably 80 to 96) wherein said process comprises:
  a) combining fatty acid (e.g., C8 to C22, preferably C10 to C18 fatty acid); a taurine and/or a taurate salt, wherein ratio of fatty acid to taurine and/or taurate salt is 1.2:1 to 10:1, preferably 1.5:1 to 8:1, more preferably 1.5:1 to 5:1; and catalyst at temperature of 200° C. or less, preferably 180° C. to 195° C.; as noted, there may be small amounts of alkali metal isethionate (as used in step (b) below) present in the initial reaction but it is minimal (preferably less than 10%, typically less than 1%, of overall isethionate which will be used (all or mostly all is used in step (b)); and
  b) upon completion of reaction (typically, this will be about 1 to 2 hours and yield of ATA is 80% or greater, preferably 81 to 100%, more preferably 82 to 95%), adding the bulk or all alkali metal isethionate to the mixture of alkyl taurate amide and residual fatty acids at temperature of 200° C. or less, preferably 180 to 195° C. (final yield of DEFI after this second step may range from 45 to 85%, preferably 55 to 85%).

Typically, no water is used in the reaction other than any minimum amount of water which is introduced as part of the raw starting material (e.g., alkali N-methyl taurine and alkali metal isethionate). Most of the water is removed during the reaction process (e.g., when heating to 180° to 200° C. in either step (a) and/or (b). In one form, the taurine or taurate salt used in step (a) is heated to 150° C. (i.e. to remove water) even before combining with fatty acid and combining at reaction conditions noted.

As can be noted, this process provides processing flexibility in that the amounts of taurine and/or taurate salt (to produce ATA) or isethionate (to produce DEFI) can be varied to produce different desired ratios of ATA to DEFI. Thus, for example, as seen in the examples relating to the Ilardi reference (reproduced Examples 26-31), ratios of DEFI to ATA in these examples ranged from 14:1 to 22:1. In our examples, ratios may range from 0.1:1 to 7:1, preferably 0.5:1 to 5:1 (0.28:1 to 2.05:1). Thus, using our process, it is possible to produce relatively much greater amounts of ATA. Further, as noted, because the ATA produced in the first part of the reaction appears to serve as an emulsifier, DEFI (the majority or all of which is produced in the second part of the reaction) can be produced at lower process temperatures (i.e., ATA acting as emulsifier helps isethionate and fatty acid react at lower temperatures in this second part of the reaction); and measured L values of DEFI/ATA produced are 80 and greater, typically 80 to 96 (i.e., there is substantially no browning).

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

The invention relates to novel processes for making mixtures of fatty acyl isethionate (e.g., direct esterified fatty acyl isethionate or "DEFI") and alkyl taurate amides. The process allows in particular for ATA to be prepared in higher yield (e.g., 80% or greater, preferably 82% or 85% and greater) while simultaneously, in final mix (because ATA made in first part of reaction acts as emulsifier and permits the bulk or total DEFI produced in the second part of the reaction to be prepared at lower temperature), in the substantial absence of browning (as measured by L value of the ATA/DEFI mixture). In some aspects of the invention, levels of ATA are quite high such that the ratio of DEFI relative to ATA is, for example, 7:1 and less, e.g., 0.1:1 to 5:1.

The invention further relates to mixtures of DEFI and ATA wherein the final ratio of DEFI to ATA is 0.1:1 to 7:1, preferably 0.5:1 to 5:1 and wherein L value of ATA demonstrates no browning (as measured by L value of ATA/DEFI mixture of 80 to 96). Preferably, the compositions are made by the process of the invention.

Finally, the invention relates to a process wherein, by controlling process parameters (particularly order of addition), lower reaction temperatures can be used (e.g, the bulk of alkali metal isethionate is added in the second step, assuming some DEFI is made in the first step; or all of the alkali metal isethionate is added, if no DEFI is made in the first step; the DEFI be made at lower temperature in the second step because ATA is acting as emulsifier), thereby providing reaction flexibility as to ratios of DEFI to ATA in final mix.

Specifically, the process of the invention comprises:
1) in a first portion of the process, combining fatty acid (e.g., C8 to 022 fatty acid); taurine and/or taurate salt (wherein ratio of fatty acid to taurine and/or taurate salt is 1.2:1 to 10:1, preferably 1.5:1 to 8:1, more preferably 1.5:1 to 5:1); and catalyst at temperature of 180° C. to 200° C.; and
2) upon completion of first portion of reaction (typically within 1 to 2 hours), adding the bulk or all alkali metal isethionate to the mixture at a temperature of 200° C. or less, preferably 180° C. to 195° C. Typically, no catalyst is used in the second step.

By "bulk or all" isethionate is meant that less than 10%, typically less than 1% of all alkali metal isethionte used in both steps (a) and (b) is actually used in step (a). Step (a) is primarily about producing sufficient ATA to act as emulsifier for the reaction of step (b), thereby allowing step (b) to be conducted at a lower temperature than previously believed needed.

The yield of ATA produced from the first step of the reaction process is typically 80% or greater, preferably 81% to 100% and can be 82% to 95%. The yield of DEFI, after the second step of the reaction, may range from 45 to 95%, preferably 55 to 95%.

While not wishing to be bound by theory, it is believed that the ATA formed in the first portion of the reaction (which is produced in relatively high yield and has substantially no browning (as measured by final L value of ATA/DEFI mixtures) functions as an emulsifier which, in turn, allows the second portion of the reaction (production of DEFI when the vast majority or all, i.e., greater than 90% to 100%, isethionate is added) to be conducted at much lower temperatures. As such, the ATA in the mixture can be retained at high yield and with no subsequent browning as noted.

Thus, a key factor for the process of the invention (which in turn allows production of novel mixtures containing relatively large amounts of ATA which is not browned) is to first prepare ATA by combining taurine and/or taurate salt with excess fatty acid at relatively low temperature (180° to 200° C.). That is, it is important that ATA be pre-produced. As noted, small amounts (less than 10%, preferably less than 5%, more preferably less than 1%) of isethionate may be produced in step (a) but this is not the main function of step (a).

The fatty acid used is typically $C_8$ to $C_{22}$, preferably $C_8$ to $C_{16}$ fatty acid. The fatty acid is typically combined with taurine (e.g., 2-aminoethanesulfonic acid) having the structure:

$RNHCH_2CH_2SO_3H$ where:

R may be, for example, hydrogen or methyl; or a taurate salt, wherein the hydrogen on the sulfate group is instead a counterion such as a sodium or potassium counterion. In theory, mixtures of the acid and salt may be used.

The fatty acid is used in excess and broadly is used at ratio of 1.2:1 to 10:1, preferably 1.5:1 to 8:1.

As indicated above, typically it is preferred to have minimum amount of water. The water is typically part of the raw starting material, for example, sodium N-methyl taurine and sodium isethionate, and the majority of the water is removed during the reaction process (for example, heating at 180° C.-190° C.). In one form of this invention, the water in the sodium N-methyl taurine is preferably removed by heating at 150° C. prior to reaction with fatty acids to form ATA.

Catalysts are typically used in the first part of the reaction, but not necessarily. The catalyst can be added in the second part. It is preferred to use catalyst in the first part of the reaction in order to maximize the yield of ATA.

A wide variety of catalysts can be employed with the present reaction. Suitable catalysts include multivalent metal ion salts or organic or inorganic compounds, strong acids and mixtures thereof. Alkali metal oxide catalysts may be used. Examples include zinc oxide, magnesium oxide and calcium oxide. Zinc oxide, a preferred catalyst, can be utilized in this invention. However, faster acting catalysts are preferred. Among the fast organic catalysts is zinc isethionate. Especially preferred inorganic zinc compounds are those selected from the group consisting of zinc sulfate, zinc sulfamate, and zinc oxide acidified with sulfamic or sulfonic acid. Mixtures of the aforementioned compounds may also be employed.

The catalyst is present from about 0.01% to about 2% (calculated e.g., as zinc or other metal ion) based on the combined weight of charged reactants. Preferably, the amount of catalyst charged will range from about 0.01 to 1%. Higher amounts of catalysts, particularly those containing zinc, are undesirable due to their detrimental effect on product qualities such as color.

After taurine and/or salt (and alkali metal isethionate, if any), fatty acid and catalyst are combined, the first portion of the reaction is allowed to run to completion. Typically, thus takes 1 to 2 hours.

At this point, the ATA is formed in a yield of 80% and greater, preferably 81% to 90% and greater.

At this point, the bulk or all (greater than 90% to 100%) of alkali metal isethionate is added to the reaction chamber (containing ATA and excess fatty acid and any small amount of DEFI which may be present). Because of the presence of ATA, the reaction between isethionate and excess fatty acid still in the reactor in this second part of the reactor is more efficient and can occur at lower temperature (e.g., 200° C. or less). This means the ATA present in the reactor, and after the final reaction, will not brown. This is measured by using an L scale wherein the L value of the final DEFI/ATA mixture is greater than 80, preferably 80 to 96, more preferably 90 to 96.

Since large amounts of non-browned ATA can be made, the ratio of DEFI to ATA can be kept not too high. Thus value of DEFI to ATA may range from or 0.1:1 to 7:1, preferably 0.4:1 to 7:1, more preferably 0.5:1 to 5:1.

As noted, the invention also provide an opportunity to control exactly what ratios of DEFI to ATA used may be used.

PROTOCOL AND EXAMPLES

Protocol for Measuring "L" Value

Color of the product is evaluated by the Hunter Lab Color Scale. This is a color scale well known to those in the art (see "Application Note", "Insight on Color", Vol. 8, No. 9 from Hunter Lab where formulae for L, a, and b, for example are defined). On the Hunter scale, the key parameter will be the L value which is a reflectance measure of brightness.

The L value of the ATA/DEFI product mixture was obtained by visual assessment/comparison and matching the color of the ATA/DEFI product mixture against standard color chips with Hunter Lab Color Scale L, a and b values. As noted, this is routine and well known to those skilled in the art of color measurement.

Repeat Examples 26-31 of Reference, Inventive Examples 1-4 and Additional Comparative Examples 1-2

In order to demonstrate how processing affects yields and mixtures of the invention which can be made, applicants note Table I below:

|  | Comparative Example 26 of U.S. Pat. No. 6,562,874 | Comparative Example 27 of U.S. Pat. No. 6,562,874 | Comparative Example 28 of U.S. Pat. No. 6,562,874 | Comparative Example 29 of U.S. Pat. No. 6,562,874 | Comparative Example 30 of U.S. Pat. No. 6,562,874 | Comparative Example 31 of U.S. Pat. No. 6,562,874 |
|---|---|---|---|---|---|---|
| Reaction Product Composition % |  |  |  |  |  |  |
| DEFI | 52.5 | 66.5 | 68 | 64.3 | 70.4 | 63.2 |
| Na Isethionate | 12.35 | 11.99 | 15.62 | 13.73 | 9.65 | 9.09 |
| Fatty Acid | 31.7 | 17.2 | 10.3 | 18.3 | 15 | 22.95 |
| N-methyl Taurine Na | 0.809 | 1 | 1.13 | 0.7 | 1.4 | 1.06 |
| ATA | 2.57 | 3.32 | 4.78 | 2.99 | 3.48 | 3.62 |
| ATA Yield % | 36.8 | 46.2 | 68.4 | 42.8 | 49.8 | 51.8 |
| DEFI Yield % | 71.1 | 90 | 92 | 87 | 95.4 | 85.6 |
| Ratio of ATA/DEFI Starting Ingredient Ratio | 1 to 20 | 1 to 20 | 1 to 14 | 1 to 22 | 1 to 20 | 1 to 18 |
| Molar Ratio of sodium N-methyl taurine to fatty acid | 1 to 16.6 | 1 to 16.6 | 1 to 16.6 | 1 to 16.6 | 1 to 16.6 | 1 to 16.6 |
| Molar Ratio of sodium isethionate to fatty acid | 1 to 1.43 | 1 to 1.43 | 1 to 1.43 | 1 to 1.43 | 1 to 1.43 | 1 to 1.43 |
| Molar Ratio of sodium N-methyl taurine to Na isethionate | 1 to 11 | 1 to 11 | 1 to 11 | 1 to 11 | 1 to 11 | 1 to 11 |
| Reaction Temperature, ° C. | 238 | 238 | 238 | 238 | 238 | 238 |
| Color (L scale) of RX product |  |  |  |  |  |  |

-continued

|  | Inventive example 1 | Inventive example 2 | Inventive example 3 | Inventive example 4 | Comparative 1 | Comparative 2 |
|---|---|---|---|---|---|---|
| Reaction Product Composition % | | | | | | |
| DEFI | 54.4 | 34.4 | 53 | 14.8 | NA | NA |
| Na Isethionate | 4.5 | 9.5 | 4.9 | 1.4 | NA | NA |
| Fatty Acid | 18.3 | 17.7 | 15.7 | 11 | 22.2 | 34.6 |
| N-methyl Taurine Na | 0.4 | 1.8 | 0.31 | 0.26 | 5.4 | 5.4 |
| ATA | 26.5 | 40.1 | 24.8 | 52.1 | 54.2 | 46.2 |
| ATA Yield % | >95 | >95 | >95 | 82 | 77.3 | 60.4 |
| DEFI Yield % | 83 | 60 | 85 | 48.4 | NA | NA |
| Ratio of ATA/DEFI Starting Ingredient Ratio | 1 to 2.05 | 1 to 0.86 | 1 to 2.14 | 1 to 0.28 | NA | NA |
| Molar Ratio of sodium N-methyl taurine to fatty acid | 1 to 5 | 1 to 3 | 1 to 5 | 1 to 1.5 | 1 to 1.5 | 1 to 1.5 |
| Molar Ratio of sodium isethionate to fatty acid | 1 to 1.67 | 1 to 1.71 | 1 to 1.67 | 1 to 3 | NA | NA |
| Molar Ratio of sodium N-methyl taurine to Na isethionate | 1 to 3 | 1 to 1.75 | 1 to 3 | 1 to 0.5 | NA | NA |
| Reaction Temperature, ° C. | <200 | <200 | <200 | <200 | 225 | 235 |
| Color (L scale) of RX product | 95.1 | 95.06 | 95.6 | 94.5 | 53.85 | 42.1 |

L value, higher L value means lighter, lower L value means darker

Inventive examples were prepared as follows:

Inventive Example Procedure

In a four necks 250 ml round bottom flask, equipped with mechanical stirrer, condenser, solvent trap/receiver and a thermocoupler/nitrogen (N2) flow inlet, sodium N-methyl taurine (12.5 g, 55% solution, 1eq.) was added. The N2 flow was set to 0.2 liters per minute (LPM). The solution of N-methyl taurine was heated to about 150° C. to remove water. The reaction temperature was increased to about 190° C., and lauric acid (42.89 g, 5 eq.) and zinc oxide (0.7 g, 0.2 eq.) were added. The reaction mixture was stirred at 190° C. for one hour.

To the above reaction mixture, sodium isethionate (19.03 g, 3 eq.) was added. The reaction mixture was stirred at 195° C. for additional 2 hours (total 3 hours of heating).

As seen from Table 1, the temperature of each of Examples 26-31 (reproduced from U.S. Pat. No. 6,562,874 to Ilardi et al.) was conducted at 238° C. At these temperatures, the yield of ATA (produced in the same reactor as DEFI) was never higher than 68.4 (Example 28). Although in general lower temperatures would be expected to give lower yield, by the process of our invention we were able both to increase yield while also avoiding browning of ATA/DEFI mixture.

The example below used the procedure from U.S. Pat. No. 6,562,874 Ilardi et al. except that the reaction temperature was conducted at 190° C. The yield of both ATA and DEFI are lower.

| Comparative Example 3 | % in Mixture in reaction product | % Yield |
|---|---|---|
| Lauric Acid | 16 | |
| C12 N-methyl taurate sodium salt (ATA) | 26.7 | 55.6 |
| N-methyl taurine sodium salt | 2.4 | |
| C12 Isethionate sodium salt (DEFI) | 20.7 | 44.8 |
| Sodium Isethionate | 20.7 | |

This demonstrates, as noted, that using previous single step process (as in Ilardi) the yields are much lower than those using the process of our invention.

By contrast, in our Inventive Examples 1-4, N-alkyl taurine was added to the reactor before addition of the bulk or all the sodium isethionate. It can be seen that yields improved from a range of 82 to greater than 95. Moreover, when isethionate was subsequently added, the temperature of the reaction could be kept at below 200° C. and there was substantially no browning (L values all greater than 94.5).

By contrast, Comparatives 1 and 2 were conducted at higher temperature in a one-step reaction. Although yields were better than Examples of U.S. Pat. No. 6,562,874 (at least based on "ATA yield %"), clearly the L values were much lower. The examples thus show that, when higher temperature is used, L values are clearly lower. Specifically, the L values are 53.85 and 42.1. Lower L value meant darker product (browning). In the inventive examples, the L values is in the 90's.

The invention claimed is:

1. A process for preparing mixtures of directly esterified fatty acyl isethionate (DEFI) and alkyl taurate amides (ATA) comprising:
   a) combining $C_8$ to $C_{22}$ fatty acid, taurine and/or taurate salt, and catalyst at temperature of 200° C. or less; and
   b) adding greater than 90 to 100% alkali metal isethionate to the mixture at a temperature of 200° C. or less; wherein the ratio of fatty acid to taurine and/or taurate salt is 1.2:1 to 10:1.

2. The process according to claim 1, wherein the ratio of fatty acid to taurine and/or taurate salt is 1.5:1 to 8:1.

3. The process according to claim 2, wherein the ratio of fatty acid to taurine and/or taurate salt is 1.5:1 to 5:1.

4. The process according to claim 1, wherein said catalyst is a multivalent metal ion salt of organic or inorganic acid, strong acid or mixture of the two.

5. The process according to claim 1, wherein said catalyst is a metal oxide catalyst.

6. The process according to claim 5, wherein said catalyst is ZnO, MgO or CaO.

7. The process according to claim 1, wherein the reaction temperature of step (a) is 180° C. to 195° C.

8. The process according to claim 1, wherein alkali metal isethionate added in step (b) is added at temperature of 180° C. to 195° C.

9. The process according to claim 1, wherein alkyl taurate amides have substantially no browning as defined by L value of DEFI and alkyl taurate amides mixtures of 80 to 96.

* * * * *